US011850069B1

(12) United States Patent
Mars et al.

(10) Patent No.: US 11,850,069 B1
(45) Date of Patent: Dec. 26, 2023

(54) WEARABLE DEVICE AND METHODS OF MANUFACTURING

(71) Applicant: Ouraring Inc., San Francisco, CA (US)

(72) Inventors: Denis Mars, San Francisco, CA (US); Simon Ratner, San Francisco, CA (US); Curt C. von Badinski, San Francisco, CA (US)

(73) Assignee: Oura Health Oy, San Francisco, CA (US)

(*) Notice: Subject to any disclaimer, the term of this patent is extended or adjusted under 35 U.S.C. 154(b) by 360 days.

(21) Appl. No.: 17/352,923

(22) Filed: Jun. 21, 2021

Related U.S. Application Data

(60) Provisional application No. 63/041,012, filed on Jun. 18, 2020.

(51) Int. Cl.
| | | |
|---|---|---|
| *A61B 5/01* | (2006.01) | |
| *A61B 5/00* | (2006.01) | |
| *G01K 1/143* | (2021.01) | |
| *G06F 21/32* | (2013.01) | |

(52) U.S. Cl.
CPC ............ *A61B 5/6826* (2013.01); *G01K 1/143* (2013.01); *G06F 21/32* (2013.01)

(58) Field of Classification Search
CPC ..... A61B 5/0008; A61B 5/01; A61B 5/02055; A61B 5/68; A61B 5/6801; A61B 5/6813; A61B 5/6825; A61B 5/6828; A61B 5/6826; A61B 2562/0271
See application file for complete search history.

(56) References Cited

U.S. PATENT DOCUMENTS

| | | | | |
|---|---|---|---|---|
| 11,324,292 | B2 * | 5/2022 | Min ..................... | A61B 5/6826 |
| 2015/0277559 | A1 * | 10/2015 | Vescovi ................. | G06F 3/017 |
| | | | | 345/173 |
| 2017/0011210 | A1 * | 1/2017 | Cheong ................. | A61B 5/681 |

* cited by examiner

*Primary Examiner* — Chu Chuan Liu
(74) *Attorney, Agent, or Firm* — Holland & Hart LLP

(57) ABSTRACT

A smart ring includes a shell having an internal surface and sidewalls define an interior, a battery within a first sector of the interior, a PCB within a second sector of the interior having components including a fingerprint sensor, a temperature sensor, a memory and a processing unit coupled to the temperature sensor and the fingerprint sensor and configured to determine whether an incoming fingerprint data is authenticated, and a potting compound disposed within the interior and encapsulating the components, wherein the potting compound forms an inner portion of the smart ring characterized by a first curved portion, a first and second flat regions within the second sector and a third region within the second sector between the first and second flat regions, wherein the fingerprint sensor is disposed below the first flat region, and wherein the temperature sensor is associated with the second flat region.

20 Claims, 5 Drawing Sheets

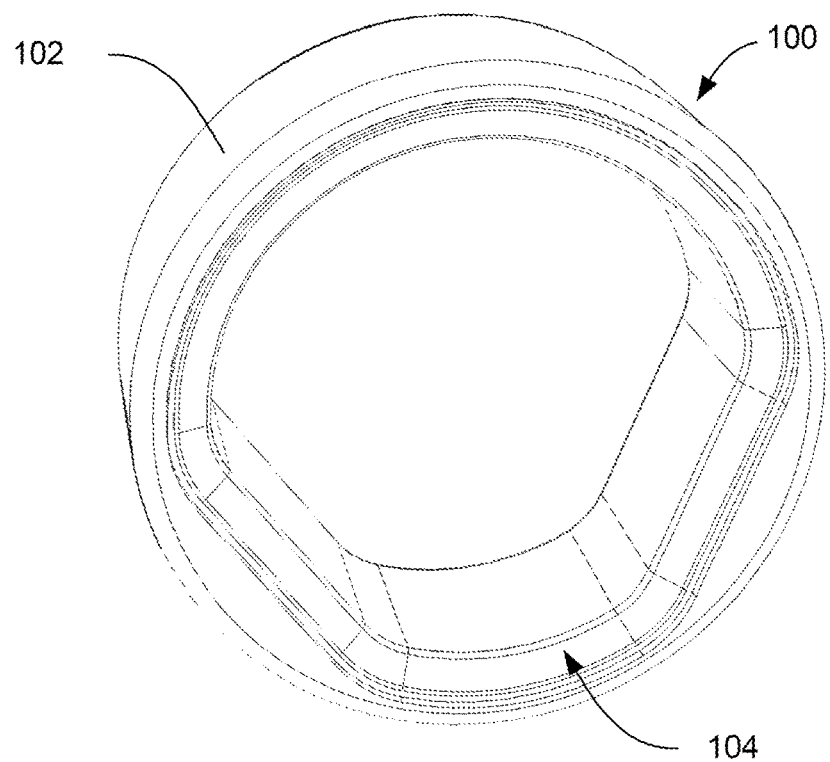
FIG. 1A
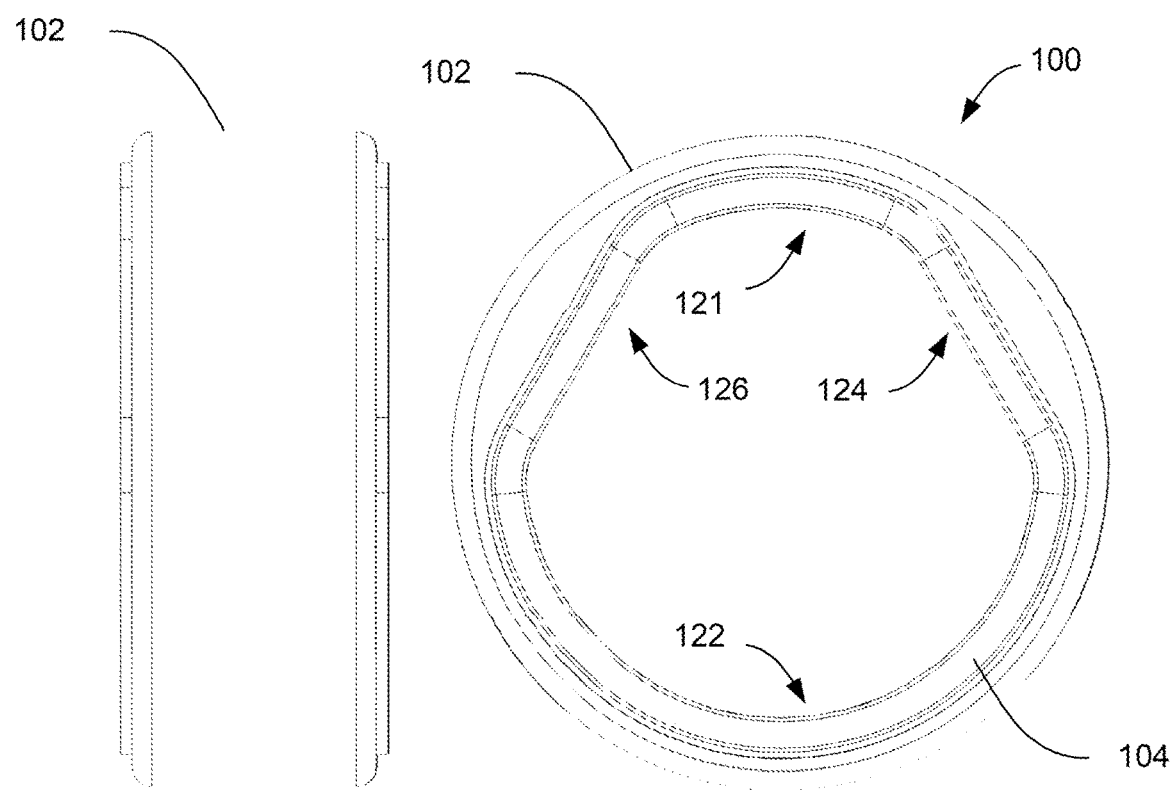
FIG. 1B
FIG. 1C

WEARABLE DEVICE AND METHODS OF MANUFACTURING

CROSS-REFERENCE TO RELATED APPLICATIONS

The present invention claims priority to and is a non-provisional of U.S. Pat. App. No. 63/041,012 filed Jun. 18, 2020, and incorporates it by reference herein, for all purposes.

BACKGROUND

The present invention relates to smart wearable devices and methods of manufacturing thereof.

An inventor of the present invention has been a pioneer in the field of smart wearable devices, specifically smart rings, since 2013. At Motiv, the first commercially successful smart ring manufacturer, miniaturization and precision manufacturing capabilities were a great challenge. Increasing the functionality of these smart rings, as described herein, presents new technical challenges that were not previously contemplated or previously solved.

What are desired are new smart wearable devices and methods for manufacturing thereof.

SUMMARY

In some embodiments, the smart ring may include an exterior O-shaped profile shell having an interior region. The exterior shell may be formed of a rigid material, such as plastic, silicone, wood, metal, ceramics, or the like. The U-shaped cross-section bounds an interior region where an electronics subassembly portion and power supply are located. In some cases, the electronics subassembly portion spans a first sector of the ring and the power supply spans another sector of the ring. The electronics sub-system may include a main control unit, wireless communications, output indicators (e.g. display, LED light, haptic generator, speaker, or the like), a biological sensor (e.g. thermometer, heart rate sensor, blood oxygen sensor, or the like), a perturbation sensor (e.g. accelerometer, gyroscope, pressure sensor, magnetic sensor, or the like), a presence sensor (e.g. capacitive, IR) and the like. In various embodiments, one or more of these components may be mounted upon a flexible or rigid printed circuit board. An over-molding compound is molded on top of the electronics subassembly portion, the power supply, and typically within the interior region. The compound forms an inner surface of the smart ring that contacts the wearer's finger.

According to one aspect, a smart ring is disclosed. One apparatus includes a round shell comprising an external surface, an internal surface, and sidewalls, wherein the external surface defines an outer diameter portion of the smart ring, and wherein the internal surface and the sidewalls bound an interior region that is characterized by a u-shaped cross-section, a curved power source disposed within a first annulus sector of the interior region, wherein the curved power source is configured to provide operating power, and a circuit board coupled to the curved power source and disposed with a second annulus sector of the interior region. In one device, a plurality of electronic components are disposed upon a circuit board including: a temperature acquisition device configured to provide a plurality of output signals in response to a heat source coupled to the temperature acquisition device, an accelerometer configured to provide perturbation signals in response to physical perturbations of the smart ring; a wireless transceiver configured to send and receive data to a smart device paired to the smart ring, a memory, and a processing unit coupled to the temperature acquisition device, the accelerometer, the wireless transceiver and the memory, wherein the processing unit is configured to determine a plurality of sensed temperatures in response to the output signal, wherein the processing unit is configured to store the plurality of sensed temperatures in the memory, and wherein the processing unit is configured to direct the wireless transceiver to output the plurality of sensed temperatures to the smart device. A device may include a potting compound disposed within the interior region and encapsulating the curved power source, the circuit board and the plurality of electronic components, wherein the potting compound forms an inner portion of the smart ring.

According to another aspect, a fabrication method is disclosed. A technique includes receiving a round shell comprising an external surface, an internal surface, and sidewalls, wherein the external surface forms an outer diameter portion of a smart ring, wherein the internal surface comprises a plurality of anchor portions, and wherein the internal surface and the sidewalls bound an interior region that is characterized by a u-shaped cross-section, and disposing a curved power source within a first annulus sector of the interior region. A process includes disposing a circuit board within a second annulus sector of the interior region, wherein the circuit board comprises a plurality of electronic components includes a temperature acquisition device, an accelerometer, a wireless transceiver, a memory. and a processing unit. A method may include coupling a curved power source to a circuit board, securing the circuit board within an interior region via a plurality of anchor portions, and disposing a potting compound within the interior region and encapsulating the curved power source, the circuit board and the plurality of electronic components, wherein the potting compound forms an inner portion of the smart ring.

According to various aspects, a smart ring is disclosed. One device may include a round shell comprising an external surface, an internal surface, and sidewalls, wherein the external surface defines an outer diameter portion of the smart ring, and wherein the internal surface and the sidewalls bound an interior region that is characterized by a u-shaped cross-section, and a curved power source disposed within the interior region and within a first annulus sector of the smart ring, wherein the curved power source is configured to provide operating power. An apparatus may include a circuit board coupled to the curved power source and disposed within the interior region and within a second annulus sector of the smart ring and a plurality of electronic components disposed upon the circuit board. The plurality of electronic components may include a fingerprint sensor configured to provide incoming fingerprint data in response to a fingerprint provided to the fingerprint sensor, a temperature sensor configured to provide a plurality of output signals in response to a heat source, a memory configured to store authorized fingerprint data, and a processing unit coupled to the temperature sensor and the fingerprint sensor, wherein the processing unit is configured to determine whether the incoming fingerprint data is authenticated in response to the authorized fingerprint data. A ring may include a potting compound disposed within the interior region and encapsulating the curved power source, the circuit board and the plurality of electronic components, wherein the potting compound forms an inner portion of the smart ring, wherein the interior portion of the smart ring is characterized by a first curved portion, a first flat region within a first portion of the second annulus sector, a second flat region within a second portion of the second annulus sector, and a third portion of the second annulus sector disposed between the first flat region and the second flat region. In some embodiments, the fingerprint sensor is disposed below the first flat region and the temperature sensor is associated with the second flat region.

According to various aspects, a method for fabricating a smart ring is disclosed. A technique may include receiving a round shell comprising an external surface, an internal surface, and sidewalls, wherein the external surface defines an outer diameter portion of the smart ring, and wherein the internal surface and the sidewalls bound an interior region that is characterized by a u-shaped cross-section, and receiving a curved power source configured to provide operating power. A process may include receiving a circuit board having a plurality of electronic components including a fingerprint sensor configured to provide incoming fingerprint data in response to a fingerprint provided to the fingerprint sensor, a temperature sensor configured to provide an output signal in response to a sensed temperature, a memory configured to store authorized fingerprint data, and a processing unit coupled to the temperature sensor and the fingerprint sensor, wherein the processing unit is configured to determine whether the incoming fingerprint data is authenticated in response to the authorized fingerprint data, and coupling the curved power source to the circuit board. A method may include disposing the curved power source within the interior region within a first annulus sector of the smart ring and the circuit board within a second annulus sector of the smart ring, disposing the round shell within a mold, and disposing a potting compound into the mold to thereby encapsulate the curved power source and the circuit board, wherein the potting compound forms an inner portion of the smart ring, wherein the interior portion of the smart ring is characterized by a first curved portion, a first flat region within a first portion of the second annulus sector, a second flat region within a second portion of the second annulus sector, and a third portion of the second annulus sector disposed between the first flat region and the second flat region. In some embodiments, the fingerprint sensor is disposed below the first flat region, and the temperature sensor is associated with the second flat region.

SUMMARY

In various embodiments, a smart wearable device may be embodied as a smart ring, smart tag, smart glasses, smart headphones, and the like. In the example below, a novel smart ring is disclosed. In various embodiments, a smart ring may include a power supply such as a lithium ion battery, lithium polymer battery, an ultracapacitor, carbon nanotube capacitor, button batteries or the like. In various embodiments, the power supply is curved in shape, as illustrated below. In the case of discrete batteries, e.g. button batteries, these batteries should also be coupled in a curved orientation, to match the curvature of the ring form factor.

In various embodiments, power management and charging circuitry is typically provided to control charging of the power supply. In some examples, charging may be facilitated by and external power source, such as an electrical source, magnetic source, radio frequency (rf) source, NFC (e.g. Qi Charger), light or laser source, heat source, or the like. In various cases, the charging circuitry may include components appropriate for the charging source, such as electrical contacts, metal coils, solar or light power conversion regions, thermoelectric generation components, or the like.

Additionally, in some embodiments of a wearable device, self-power-generation components may be included that generate power in response to movement of the wearable device, e.g. smart ring, bio patch, wrist device, etc. Some examples may include a movable magnet or magnetic liquid moving that passes back and forth through a coil as the person walks to generate electricity. Other examples may include a charged liquid passed back and forth through a ferromagnetic material that generates the electricity. In some cases, a channel or tube for the liquid may span only a sector of the ring, and in other cases, the channel or tube may run fully around the ring. In some embodiments, the tube may be tapered in the vicinity of the energy producing coil or ferromagnetic material. Accordingly, as the user moves, the liquid may move in the tube at a first velocity, and as the liquid reaches the tapered section, the liquid velocity may increase to a higher, second velocity. In this example, the higher velocity liquid may induce greater electricity generation. In various embodiments, usable ranges of viscosity of the liquid may be determined based upon power requirements and predicted user motion.

In the embodiments below, other functional elements may include a microcontroller unit having a wireless transmitter. In various embodiments, the microcontroller unit may perform identification functionality, e.g. providing a non-permanent, ephemeral IDs output, communicating with authentication services, interfacing with other smart devices, interfacing with identity reader devices, facilitating other types of authentications, such as FIDO 2, or the like. Examples of wireless transmissions that may be supported includes Bluetooth, ultrawide band (UWB), Zigbee, rf, WIFI, cellular, 4G, 5G, and the like.

In some embodiments, memory elements may be provided for storage of data, computer code executable upon the microcontroller; a secure element for storage of secure data, such as encryption keys, tokens associated with financial accounts (e.g. credit cards, debit cards, etc.), tokens provided by embodiments of the present invention, described above, and the like. In some cases, NFC communication is provided enabling financial transactions using data stored within the secure element and point of sale (POS) terminals, and the like.

In various embodiments, a number of sensors may be provided to sense a variety of parameters associated with the user. In some embodiments, a temperature sensor is provided to sense the temperature of the user adjacent to the wearable device. In some examples, a temperature sensor may utilize: a thermocouple, a thermistor, a resistor temperature detector, a semiconductor sensor, an infrared sensor, or the like. Depending upon the embodiment, one or more temperature conductive contacts, e.g. metal, may be used; an infrared transparent (or substantially transparent) covering may be disposed above an infrared sensor; and the like.

In other embodiments, a heartbeat, a blood oxygen sensor, or the like may be provided, typically based upon reflection or transmission on or transmission of LED light relative to the user (e.g. finger, earlobe, ear canal, temple, etc.), to monitor the heartbeat, heartbeat pattern, or the like of the user. Other types of biometric sensors may also be provided, such as a blood-vessel sensor, a fingerprint sensor, and the like. In one embodiment, a specific region of the smart ring may be electrically insulated from other portions of the smart ring that contact the user's fingers. In such embodiments a user may place a finger from their other hand upon the specific region to enable the ring to sense a user's EKG, ECG, or the like. In various embodiments, these types of biometric sensors may be used for authenticating the user on the device. For example, using a capacitive, optical sensor, or the like on the interior of the ring, the smart device (e.g. smart ring, smart earbud, smart glasses) may be locked every time the device is taken off, and not unlocked until the proper biometric credentials are presented. In other embodiments, various biometric data may be used for health monitoring purposes, as disclosed herein.

In some embodiments, additional sensors may include accelerometers, gyroscopes, magnetometers, pressure sensors, or the like, that capture movements of the smart device. In various embodiments, the captured perturbation data may be used for a number of functions. One function is the capturing of user movements and recognition of these movements as one or more pre-defined gestures. Upon determination of the gestures, the smart ring may perform specific functions, direct an external device to perform a function, or the like. In other embodiments, the captured perturbation data may be used to determine biometric characteristics of the user, e.g. gait, stride length, and the like.

In some embodiments, sensors described above, as well as additional sensors may be used for the user to select different modes of operation and to interact with the smart devices. As merely an example, a pressure sensor may detect a user pressing upon the smart device; a capacitive sensor may detect whether the user is wearing the smart device; a microphone may detect spoken user commands; one or more physical buttons may detect a user depressing a button; and the like. In other examples, a magnetic sensor may determine orientation of the ring with respect to a global magnetic field, the presence and orientation of a local magnetic field (device) with respect to the ring, or the like. In some embodiments, any number of outputs may be provided to give the user feedback. Examples of user outputs includes, a micro display (e.g. OLED), one or more status LEDs, vibrational (haptic) feedback, audio outputs, SMS output and the like. In some embodiments, a smart ring is disclosed, as illustrated below.

BRIEF DESCRIPTION OF THE DRAWINGS

In order to more fully understand the present invention, reference is made to the accompanying drawings.

FIGS. 1A-1H illustrate embodiments of the present invention;

In order to more fully understand the present invention, reference is made to the accompanying drawings. Understanding that these drawings are not to be considered limitations in the scope of the invention, the presently described embodiments and the presently understood best mode of the invention are described with additional detail through use of the accompanying drawings.

DETAILED DESCRIPTION

Figure 1D:
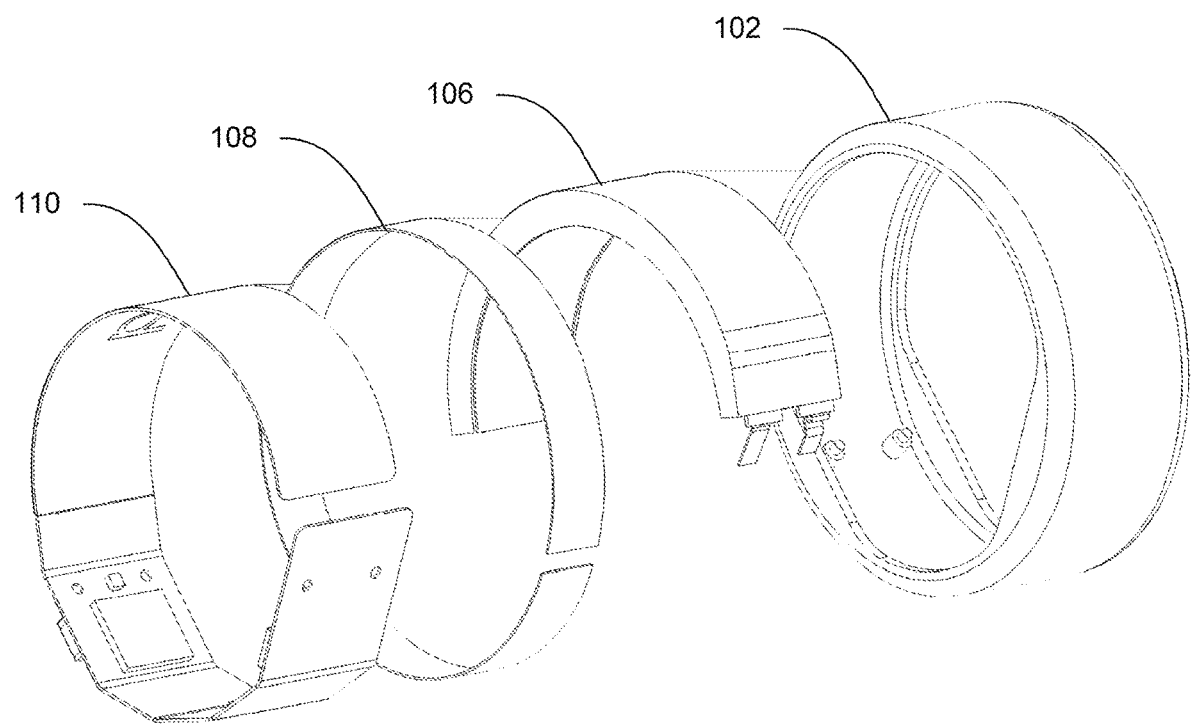

FIGS. 1A-1G illustrate various views of some embodiments of the present invention. More specifically, FIG. 1A illustrates a perspective view, FIG. 1B illustrates a typical side view, and FIG. 1C illustrates a top/bottom view. In these figures, a smart ring 100 includes an exterior shell portion 102 and an interior portion 104, as will be discussed below. As can be seen, the shape of exterior shell portion 102 may circular, semi-circular, or the like, and the interior shape of interior portion 104 may have curved portions 121 and 122 and less curved portions 124 and 126 (e.g. flat, larger radius of curvature than portions 121 or 122, etc.). In some embodiments, less curved portions 124 and 126 may include substantially flat regions. In other embodiments, less than two, or more than two curved portions (e.g. 124 and 126) may be used in the design, for example, the interior profile of the ring may include one less curved portion, three less curved portions, four less curved portions, or the like.

In various embodiments, as can be imagined by one of ordinary skill in the art, the less curved portions 124 and 126 disclosed here push into the skin of a wearer and provides more substantial contact regions between smart ring 100 and a user's finger. As illustrated below, in some embodiments, a fingerprint sensor, a capillary sensor, or other biometric acquisition device may be associated with one of such flat (or less curved) regions. It is believed that a sensor, disposed in such a flat region, will then be able to obtain a higher quality biometric sample. Additionally, in some embodiments, a temperature sensor, e.g. an infrared sensor, a thermal conductive sensor, or the like may be associated with the other of such flat regions. Again, it is believed that a higher finger to sensor contact may be able to obtain higher quality temperature readings. Still further, in some embodiments, by locating a flat NFC antenna within the less curved, e.g. flat, regions will allow higher quality NFC communications between the smart ring and an external NFC device.

In various embodiments, exterior shell portion 102 may be made of any suitable material, such as: plastic, ceramic, metal, silicone, titanium, wood, or the like. Additionally, interior portion 104 may be made of any suitable material such as: plastic, ceramic, metal, silicone, titanium, wood, epoxy, latex, or the like. As will be described below, portions 102 and 104 may be opaque, transparent, or translucent.

FIG. 1D illustrates an embodiment of an exploded view of a smart ring including exterior shell portion 102, a power source 106, a light pipe 108 and an electronics assembly 110. These elements will be separately discussed below.

In some embodiments, a light pipe 108 may extend substantially around the circumference (e.g. 330 degrees to 360 degrees), or may extend around a portion of the circumference (e.g. <360 degrees, 180 degrees to 270 degrees, 90 degrees to 180 degrees, or the like). In some cases, light pipe may be disposed substantially adjacent to an interior surface of exterior shell portion 102 (on the larger radius of curvature surface of power source 106). In these embodiments, light output by light pipe 108 may be configured to be output through exterior shell portion 102 or the circular edge (e.g. same edge as sidewalls 114 in FIG. 1F) of exterior shell portion 102. In other cases, light pipe may be disposed closer to interior portion 104 (e.g. on the smaller radius of curvature surface of power source 106. In these embodiments, light output by light pipe 108 may be configured to be output through interior portion 104 or the circular edge (e.g. same edge as sidewalls 114) of exterior shell portion 102.

In various embodiments, light pipe 108 (sometimes known as a light guide) may be optically coupled to one or more light sources (e.g. LEDs) provided on electronics sub-assembly 110. In some cases, the light sources may be visible light sources (e.g. red, blue, green, etc.) and in other embodiments, the light sources may be UV, IR, or the like. In some embodiments, light pipe may include photoluminescent quantum dots, fluorescent materials, or the like, that may convert incoming radiation to radiation within a visible spectrum.

Figure 1E:
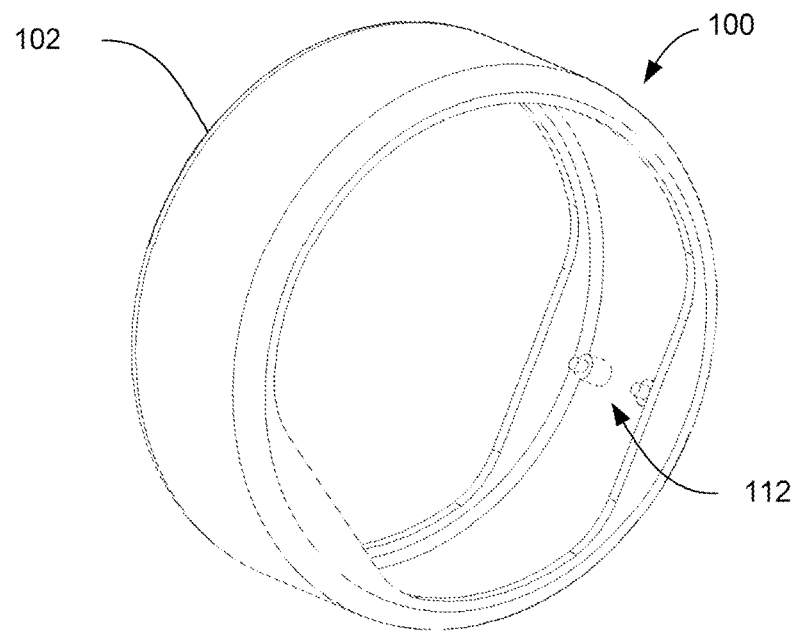

FIG. 1E illustrates an embodiment of an exterior shell portion. In some embodiments below, exterior shell portion 102 may be manufactured from a material such as: injection molded plastic, a metal, silicone, or the like. They may also be machined from blocks of material, such as ceramic material, and the like. In some cases, the material may be translucent, clear, opaque. In other cases, portions of exterior shell portion 102 may be formed from more than one material, having different textures, light transmission capability, or the like.

As illustrated in FIG. 1E, in some cases, alignment pins 112 may be provided and may be monolithically formed with exterior shell portion 102. In other cases, alignment pins 111 may be attached, glued, or the like to exterior shell portion 102. In other embodiments, other types of alignment structures may be used, such as alignment tabs, holes, or the like. In still other embodiments, alignment structures may not be needed. As will be illustrated below, alignment pins maybe be attached to the interior of exterior shell portion 102 via one or more subframes.

Figure 1F:
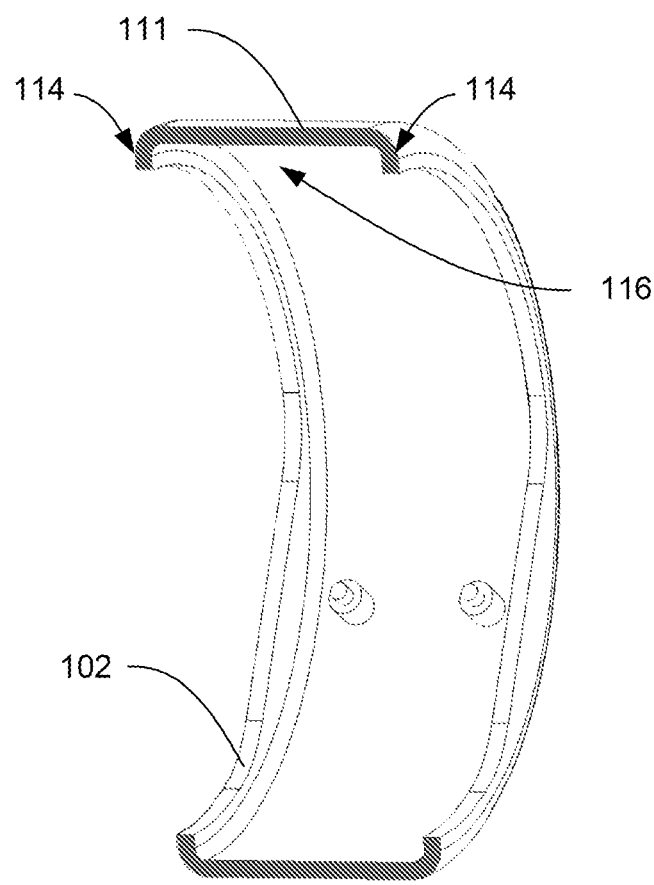

FIG. 1F illustrates a cross-section of an exterior shell portion of some embodiments. In the embodiment of the cross-section below, exterior shell portion 102 includes a rounded exterior surface 111, and side walls 114 that may be formed of the same material. In other embodiments, these portions may be separate. In this example, round exterior surface 111 and sidewalls 114 form an interior region 116, into which components 106-110, and the like may be placed. In some embodiments, the interior of exterior shell portion 102 need not be smoothly curved of uniform thickness, but portions may have varying thickness or geometry, portions may be scribed, etched, or formed with geometric features (e.g. company logo, a symbol (e.g. a check mark)), or the like. In cases where there is a light source (e.g. light pipe 108) disposed within interior region 116, light provided by light pipe 108 may be non-uniformly output through exterior shell portion 102 on account of the differences in material thicknesses, geometry, or the like. As an example, a company logo, a symbol (e.g. a check mark, an X mark), or the like may not be visible, until such structures are back-lit by light pipe 108, or any other light source (e.g. LED) disposed within interior region 116.

Figure 1G:
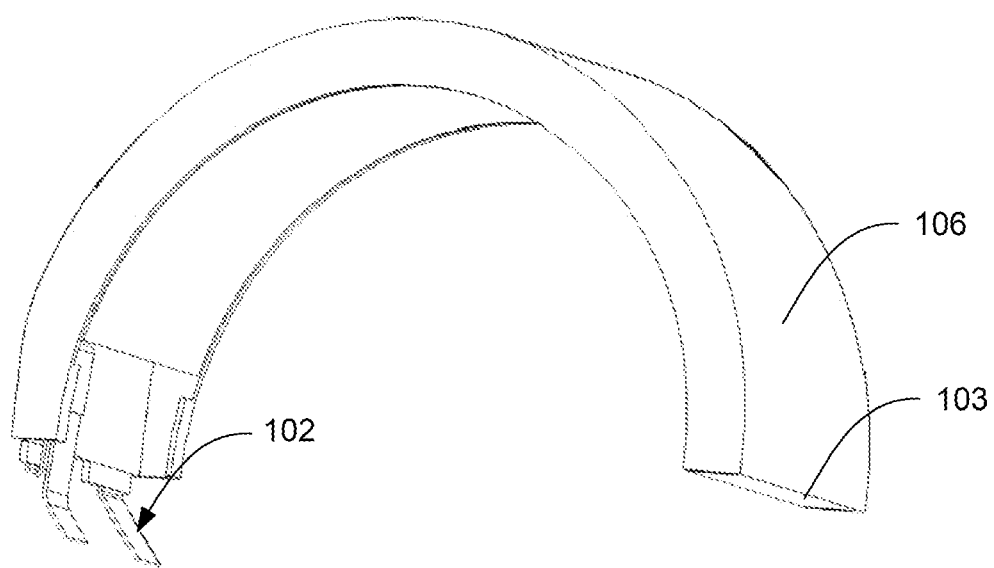

FIG. 1G illustrates an embodiment of a power source 106. In various examples below, power source 106 may be formed in a curved shape, substantially matching the curve of a portion of interior region 116. In the following example, power source 106 may be approximately in an annulus shape, having a sector angle from 90 to 180 degrees, 45 to 270 degrees, or the like. In various embodiments, power source may be a lithium ion battery, a lithium polymer battery, a carbon-nanotube storage device, an ultracapacitor, or any other type of conventional battery (e.g. a series of button batteries). As shown in this example, power source 106 may include power connections 118, formed or a metal such as nickel, copper, silver, or the like.

Figure 1H:
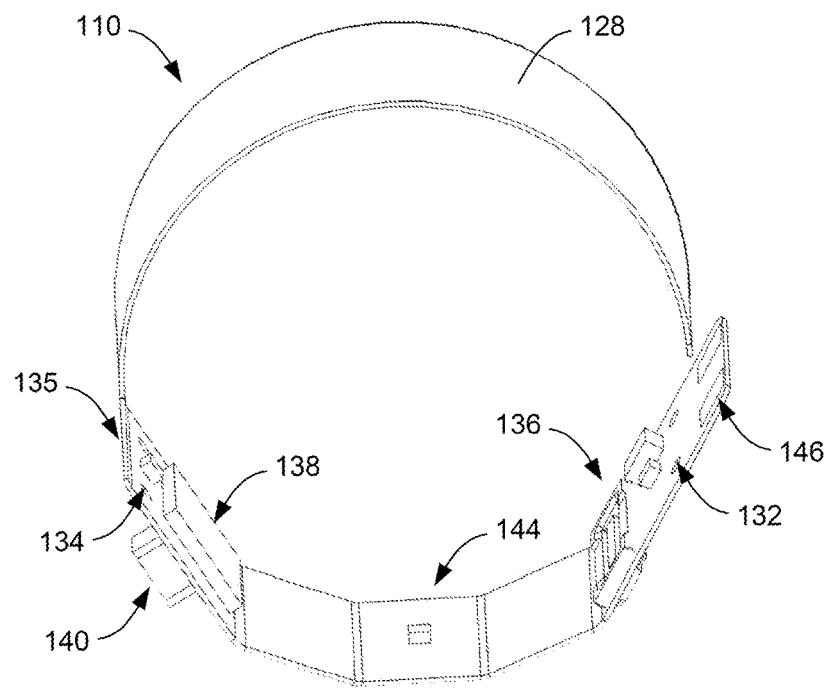

FIG. 1H illustrates an embodiment of an electronic subassembly. In this example, electronics subassembly 110 includes an adhesive portion 128, a printed circuit board (PCB) 130, and a number of electronic components. In this embodiment, adhesive portion 128 is used to couple electronics subassembly to the interior of exterior shell portion 102. In various embodiments, printed circuit board 130 may be a flexible PCB (e.g. Mylar based), may include rigid PCBs coupled via flexible PCBs, or the like. As can be seen, PCB may include round holes 132, 134, or other geometric shaped holes, or may include slots, indents, or the like. These geometric features 132, 134, or the like may be used to physically secure PCB 130 within exterior shell portion 102. More specifically, alignment pins 112 (or other types of alignment geometry) may be disposed through holes 132, 134 (or other types of alignment geometry) to reduce the rotation of electronics subassembly 110 within exterior shell portion 102 during an assembly or manufacturing process.

In various embodiments, electronics subassembly 110 may include a number of electronic components, such as a temperature sensor 136, a presence sensor 144, a biometric data reader 138, and an NFC power/communications device 140. Other types of electronics, not specifically called-out may include, a processor, a short-range wireless transceiver, an accelerometer, a gyroscope, a magnetometer, a heartbeat sensor, audio output devices, audio input devices, LEDs and the like.

In various embodiments, temperature sensor 136 may be based upon optical IR, thermocouple, thermistor or other temperature sensor. Additionally, presence sensor 144 is configured to determine whether a person is wearing smart ring 100. In various embodiments, presence sensor 144 may be a capacitive sensor, a heat sensor, a pressure sensor, optical sensor, or the like. In various embodiments, biometric data reader 138 may be a fingerprint sensor, a blood-vessel imaging device, a heartbeat sensor, or the like. These devices may be imaging devices, ultrasonic devices, or the like. It is contemplated that biometric data reader 138 is used to acquire biometric data unique to the user.

In various embodiments NFC device 140 may include an NFC interface along with associated processing capability. In some embodiments, NFC device 140 may be used for a number of functions including: receiving data from an external NFC device, sending data to an external NFC device, receiving power from an external NFC device, or the like. As examples, NFC device 140 may be used to receive data or queries from another NFC device, and to query or send data (e.g. an identifier, temperature status data, etc.) to another NFC device. Additionally, in some embodiments, NFC device 140 may support charging of smart ring 100 via an NFC wireless charging infrastructure, such as Qi charging, wireless charging (WLC) specification, or the like.

In some embodiments, power connections 118 of power source 106 are coupled to tabs 146, as illustrated below. In some embodiments, tables 146 and power connections 118 may be spot welded together, avoiding a separate soldering process. In other embodiments, tabs 146 may be disposed near holes 134, and power source 106 may run the same direction as adhesive portion 128.

In some embodiments, when assembled together, power source 106 and electronics subassembly 110 may be configured in a "C" shaped structure. In various embodiments, after assembly, the gap 147 in the C shaped structure, for example between portion 103, FIG. 1G and portion 135, FIG. 1H, is physically lessened, closed or overlapping (sometimes forming an O-shaped structure) by pressing down upon power source 106 and up upon electronics subassembly 110. The combined structure is then inserted into exterior shell portion 102, i.e. over sidewalls 114, aligned to alignment structures 113, and then allowed to expand back into the C shaped structure. More specifically, alignment structures 112 align to alignment portions 132 and 134, and then adhesive portion 128 adheres to the inner wall of the exterior shell portion 102 in this step. The partially formed smart ring is thus formed.

In various embodiments, the partially formed smart ring is disposed within a mold and then an encapsulant material is over-molded upon the partially formed smart ring. In some embodiments, the material may filling interior region 116, optionally including both sides of electronics subassembly, power source 106, and the like. In some cases, one or more sets of electrodes, windows, or the like may not be encapsulated by the material, and may remain exposed to the interior of smart ring 110. In some examples, the windows may be used for fingerprint sensors, heartbeat sensors, blood vessel (e.g. capillary) sensors, or the like, and electrodes used for charging, for determining temperature, for determining electrical characteristics of the user, or the like.

In various embodiments, the encapsulant material may be silicone, epoxy, latex, plastic, or the like. The encapsulant material may be opaque, transparent, translucent or the like.

Figure 2:
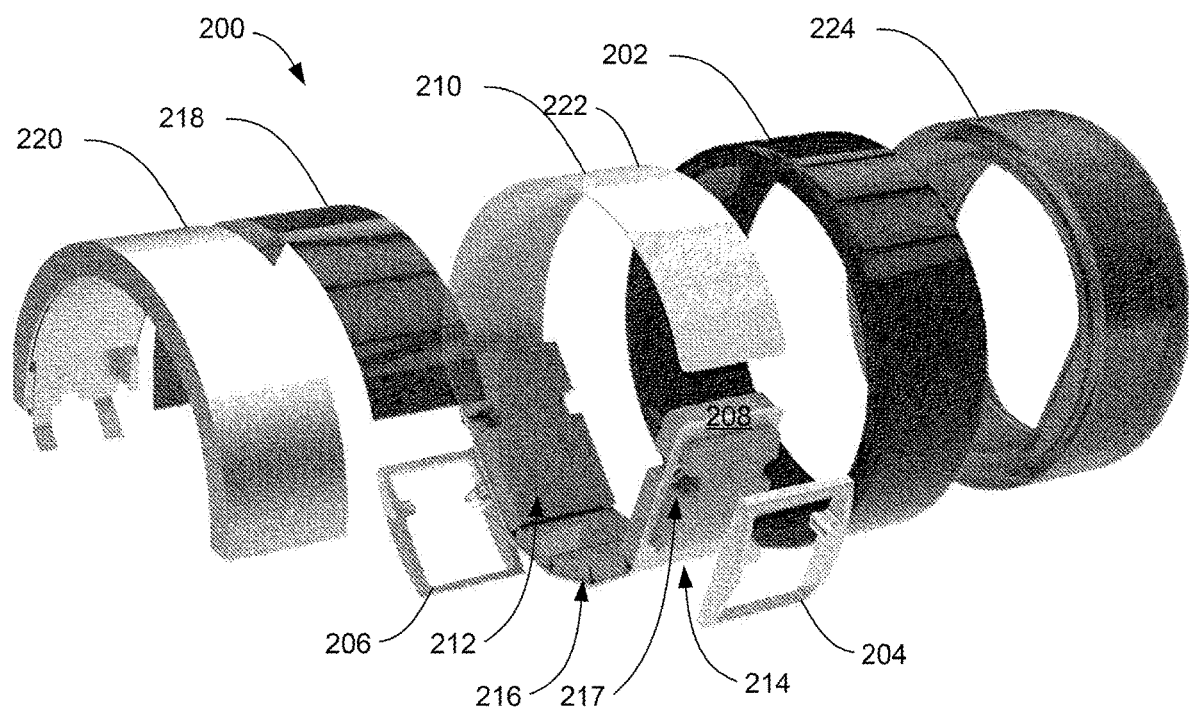
FIG. 2 illustrates additional embodiments of the present invention.

FIG. 2 illustrates additional embodiments of the present invention. This embodiment of a smart ring 200 may include: an exterior shell portion 202 formed similar to exterior shell portion 102, i.e. having side-walls. In this embodiment, alignment frames 204 and 206 are illustrated. Alignment frames 204 and 206 may be adhered to an inner wall of exterior shell portion 202 using any conventional adhesive, before the electronics components are placed within exterior shell portion 202. Frames 204 and 206 may have similar alignment or registration functionality to the alignment structures 112 illustrated in the above figures.

In some embodiments, alignment frames 204 and 206 may be made of a metal that is attracted to magnets, e.g. includes Nickle, Iron, Cobalt metal, typically in an alloy form. A charger system for smart ring 200 may include one or more magnets that are attracted to frames 204 and/or 206 allowing for a secure contact for charging or data transfer. For example, charging pins on smart ring 200 may then be aligned to charging pins on a dock, an NFC antenna or wireless charging coil in smart ring 200 may then be aligned to an NFC antenna or charging coil on a dock, and the like.

Also shown in this example is an electronics subassembly 210 including a number of electronic components coupled to a flexible printed circuit board 208 (e.g. Mylar or other polyester film). Similar to the above, electronic components may include a temperature sensor 214, a presence sensor 216, an NFC interface 212, and the like. In other embodiments, other components may include a processor, a wireless transceiver (e.g. Bluetooth, ultrawide band (UWB), ZigBee, WIFI), an accelerometer, a gyroscope, a magnetometer, an altimeter, LED devices, and the like.

In this embodiment, during an assembly process, notches, e.g. 217, in electronics subassembly 210 are used to receive notches in alignment subframes 204 and 206 thereby inhibiting electronics subassembly 210 from rotating within exterior shell portion 202.

In some embodiments, a material 218 may be provided between electronics subassembly 210 and power source 220. Accordingly, the ordering of materials may be, power source 220, material 218, adhesive portion of electronics subassembly 210, exterior shell portion 202. In some embodiments, material 218 may be formed of a ferrite material to form a ferrite reflector structure, and an additional NFC antenna 222 for the NFC device may be disposed on flex PCB 208 in the adhesive region. In such embodiments, the ferrite reflector helps to extend the range of NFC antenna 222, and helps isolate NFC antenna 222 from power source 220.

In the illustrated embodiment, material 224 represents the over-molded material that encapsulates electronics sub-assembly, power supply 220, and the like within exterior shell portion 202, and form an interior region of smart ring 200. Similar to the above, material 222 used may include silicone, epoxy, plastic, or the like, and may be somewhat transparent, translucent, opaque, or the like.

In various embodiments, a smart wearable device may be embodied as a smart ring, smart tag, smart glasses, smart headphones, and the like. These devices may be electrically charged through a standardized port (USB-C, USB, or the like), may be wirelessly charged by NFC signals, rf or magnetic signals, may be wirelessly charged by solar or laser light, and the like. Additionally, in some embodiments, self-charging capability, e.g. heat differential, and the like, may also be included In some embodiments, two smart rings may worn by a user. In these examples, gestures using both hands of a user may be used for providing instructions for the smart rings, smart devices coupled with the smart rings, or other external computing device. In some examples, when a user moves both of their hands away from or towards each other, the gesture that is interpreted is a zoom-in or zoom-out command for an external display device; when a user moves a right hand towards or away the left hand, while maintaining their left hand stationary (detected via accelerometers, etc.), the gesture that is interpreted is a next or previous command for an external computing device (e.g. next page or previous page, next track or previous page, next image or previous page, next document or previous document, pan right or pan left, etc.); and the like. In light of the present patent disclosure, one of ordinary skill in the art will recognize many other functions and gestures with two hands that are within the scope of other embodiments of the present invention.

In some embodiments, the biometric data, e.g. heartbeat data, user temperature data, blood oxygen, or the like, as well as perturbation data, e.g. accelerometer data, pressure data, gyroscopic data, and the like may be uploaded to a paired smart device for further processing. In some examples, the paired smart device may be a smart phone, computer, tablet, or the like. In various embodiments the paired smart device may determine whether the user's biometric data exceeds particular criteria, e.g. elevated heart rates, elevated temperatures, reduced blood oxygen, increased blood pressure, or the like. Such abnormal biometric data readings may indicate that the user is not healthy.

In various embodiments, the perturbation data is also processed by the paired smart device to help reduce the incidences of abnormal biometric notifications. For example, for a user, an elevated heartbeat rate or temperature may be due to the user working out, running, or the like. In such cases, an accelerometer, gyroscope, or the like will typically register strenuous and possible repetitive motions. Accordingly, a using application such as a learning algorithm, or the like running upon the paired smart device, it may recognize that when it senses increased heartrates or high temperatures along with high magnitude accelerations, the user is exercising and it does not indicate that the user is unhealthy. Other cases where the user may have elevated biometric readings along with high magnitude accelerations may include the user at an amusement park, participating a motor sport, or the like. As above, such cases should not typically indicate a health anomaly. As merely another example, a reduction in user blood oxygen saturation (biometric data) might be accompanied by an elevation gain (perturbation data). In such cases, the user may be driving or hiking up a mountain, and the perturbation data (e.g. elevation) may be determined by a barometer, GPS-based map elevation, or the like. In this situation, the biometric data and the perturbation data should not normally indicate a health anomaly.

In contrast to the above, if a user's temperature or heart rate increases above a certain threshold in the middle of the night, without substantial perturbation data, the smart phone may indicate a health anomaly. Also, if a user's blood oxygen saturation decreases by a certain percentage or below an absolute percentage, without substantial perturbation data, the smart phone may also indicate a health anomaly. In light of the above, other biometric/perturbation pairs may be used by the smart device to indicate whether the user may have a health anomaly or not.

In other embodiments, the biometric data, e.g. heartbeat data, user temperature data, gait data, and the like may be captured over days, weeks, or months and uploaded to a paired smart device for further processing. In various embodiments, the paired smart device is a smart phone. The captured data may be used by a smart phone, or by a back end cloud service to determine a baseline model for the biometric data for the user, e.g. using machine learning or artificial intelligence libraries (TensorFlow). In particular, for a first period of time while the user is healthy and going about their day normally, captured biometric data may be processed by an artificial intelligence or machine learning processes to determine a user model for the biometric data. In some examples, if the user washes their hands in cold water or hot water, the sensed user temperature should spike down or up, respectively, before returning to normal. Temperature models are expected to ignore such short-term perturbations in temperature readings. In other examples, if the user goes runs three-times a week, the sensed user heartbeats should be elevated for that period of time and for some time afterwards. Additionally, running may be determined by an accelerometer during the same time period. Heart rate baseline models are expected to also ignore or deemphasize these short-term perturbations in heartbeat data, especially if there is high accelerometer perturbations at the same time. In various embodiments, multiple models may be determined and stored in the cloud-based server or on the paired smart phone.

Subsequently, as the smart device captures new biometric data throughout the day, these new biometric data readings may be compared against one or more models (e.g. historical models) to determine if there are deviations from the models. In various embodiments, it is contemplated that the paired smart phone or the smart wearable (e.g. ring, earbuds, glasses, etc.) may perform the matching processes. In some cases, the baseline biometric models may be periodically updated, for example, on a rolling basis for the past few weeks, months, or the like.

In some embodiments, if the smart wearable device, or smart device paired to the smart wearable device determines that the newly captured user data (e.g. temperature, heartbeats, blood oxygen saturation, gait, or the like) is consistent with the user's historical model for a certain duration of time, e.g. 7 days, 14 days, or the like, the smart wearable device may provide a first indication to the user, e.g. display a green color for an LED, whereas if the newly captured data is inconsistent with the user's historical model, e.g. elevated temperature, elevated heartbeat rate, or the like, the smart wearable device may provide a second indication to the user, e.g. display a yellow color for the LED.

Additionally, in various embodiment, when coupled to an identity reader device, coupled to a controlled access point, an authentication server, the status (healthy or not-healthy) of the newly captured data may be provided. As an example, when coupled to a device (e.g. presence sensing identity reader device, authentication server, other smart device), if the new user data is inconsistent with their model, the smart device may send a yellow flag to the other device. In some examples, if an authorized employee is attempting to enter a building, but a yellow flag is provided by their smart ring, entry may be denied. For example, the identity reader device may receive the flag and although a valid identification token to enter is provided, the identity reader may not direct peripheral device (e.g. door, gate, elevator, or the like) to open. In other examples, in the case of third-party transportation, if the smart ring provides a yellow flag, a taxi or hired car may be denied, boarding of a vessel (e.g. ship, airplane, train) may be denied. In various embodiment, in order to reduce the chance of the user simply taking off or turning off their smart device, boarding, renting, or the like may require a valid electronic token, and a healthy indication, as described above.

In various embodiments, in a retail establishment, restaurant or the like, a kiosk may be provided that indicates the status of users within that facility. For example, if all of the servers have smart rings, or the like, and for every day during the previous two weeks, the user's biometric data (e.g. temperature) is consistent with their historical model, the kiosk may show names of the servers and green lights next to their name. In this way, a user entering the facility may have a certain level of confidence that the establishment is safe. Additionally, for every user in the facility having a smart ring and who is consistent with their historical models, additional green lights may be displayed on the kiosk. Accordingly, if a crowded bar has 100 green lights, a user may feel safer visiting that establishment.

In various embodiments, if the user's current readings do not match the user's historical model (e.g. a baseline model), the smart device may also contact a third party, e.g. a community health server, a company HR administrator, or the like. In various embodiments, the readings of the user may be based upon temperature, heart rate, blood oxygen saturation, blood pressure, or the like. Additionally, the historical model may be based upon any of such user readings (e.g. temperature, heart rate, etc.) when the user is healthy. This healthy state data may be processed by machine learning algorithms on a smart phone, in the cloud, or the like to determine a baseline model for the reading (e.g. a baseline temperature model, a baseline blood oxygen saturation model, etc.) Typically, these models may first be based upon a generic model (i.e. machine learning from data from hundreds or thousands of users) and may then be customized for each user, based upon machine learning algorithms using the specific readings, characteristics, physiology for the user. Over time, a user's baseline models may vary based upon additional machine learning algorithms, for example because the user loses weight, the user exercises more, the user develops a health condition, and the like.

In response, a smart device paired to the smart ring or a third party server may contact the user, via e-mail, text, SMS, phone call, vibration, or the like to communicate the anomalies or deviations from a baseline model. In some embodiments, the indication may be used to restrict a user from entering certain locations or using certain services. For example, if the smart ring is coupled to an identity reader infrastructure provided by the assignee of the current provisional application, authorization by an authentication server may be denied, a computer login may be denied, and the like, when there is a user health deviation or anomaly.

Figure 3:
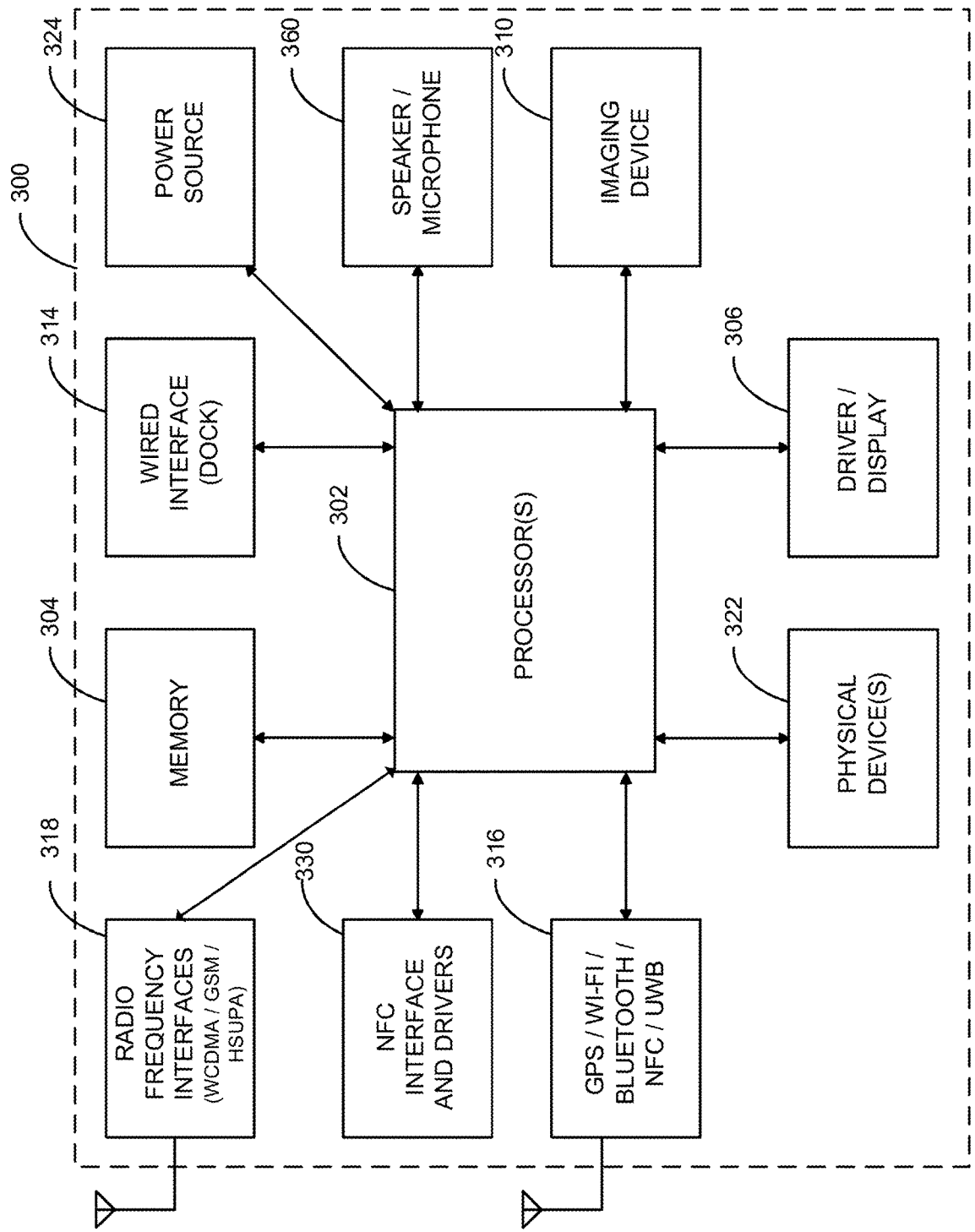
FIG. 3 illustrates additional embodiments of the present invention.

FIG. 3 illustrates a functional block diagram of various embodiments of the present invention. More specifically, it is contemplated that from user smart devices (e.g. smart wearable devices, smart phones, tablets), to laptops, to cloud-based servers, etc. may be implemented with a subset or superset of the below illustrated components.

In FIG. 3, a computing device 300 may include some, but not necessarily all of the following components: an applications processor 302, memory 304, a display 306, an image acquisition device 310, audio input/output devices 312, and the like. Additional communications from and to computing device 300 can be provided by via a wired interface 314 (e.g. dock, plug, controller interface to peripheral devices); a GPS/Wi-Fi/Bluetooth interface/UWB 316; an NFC interface (e.g. antenna or coil) and driver 318; RF interfaces and drivers 320, and the like. Also included in some embodiments are physical sensors 322 (e.g. (MEMS-based) accelerometers, gyros, magnetometers, pressure sensors, temperature sensors, bioimaging sensors etc.).

In various embodiments, computing device 300 may be a computing device (e.g. Apple iPad, Microsoft Surface, Samsung Galaxy Note, an Android Tablet); a smart phone (e.g. Apple iPhone, Google Pixel, Samsung Galaxy S); a portable computer (e.g. netbook, laptop, convertible), a media player (e.g. Apple iPod); a reading device (e.g. Amazon Kindle); a fitness tracker (e.g. Fitbit, Apple Watch, Garmin or the like); a headset or glasses (e.g. Oculus Rift, HTC Vive, Sony PlaystationVR, Magic Leap, Microsoft HoloLens); a wearable device (e.g. Motiv smart ring, smart headphones); an implanted device (e.g. smart medical device), a POS device, a server or the like. Typically, computing device 300 may include one or more processors 302. Such processors 302 may also be termed application processors, and may include a processor core, a video/graphics core, and other cores. Processors 302 may include processor from Apple (A13, A14), NVidia (Tegra), Intel (Core), Qualcomm (Snapdragon), Samsung (Exynos), ARM (Cortex), MIPS technology, a microcontroller, and the like. In some embodiments, processing accelerators may also be included, e.g. an AI accelerator, Google (Tensor processing unit), a GPU, or the like. It is contemplated that other existing and/or later-developed processors/microcontrollers may be used in various embodiments of the present invention.

In various embodiments, memory 304 may include different types of memory (including memory controllers), such as flash memory (e.g. NOR, NAND), SRAM, DDR SDRAM, or the like. Memory 304 may be fixed within computing device 300 and may include removable (e.g. SD, SDHC, MMC, MINI SD, MICRO SD, CF, SIM). The above are examples of computer readable tangible media that may be used to store embodiments of the present invention, such as computer-executable software code (e.g. firmware, application programs), security applications, application data, operating system data, databases or the like. Additionally, in some embodiments, a secure device including secure memory and/or a secure processor are provided. It is contemplated that other existing and/or later-developed memory and memory technology may be used in various embodiments of the present invention.

In various embodiments, display 306 may be based upon a variety of later-developed or current display technology, including LED or OLED status lights; touch screen technology (e.g. resistive displays, capacitive displays, optical sensor displays, electromagnetic resonance, or the like); and the like. Additionally, display 306 may include single touch or multiple-touch sensing capability. Any later-developed or conventional output display technology may be used for embodiments of the output display, such as LED IPS, OLED, Plasma, electronic ink (e.g. electrophoretic, electrowetting, interferometric modulating), or the like. In various embodiments, the resolution of such displays and the resolution of such touch sensors may be set based upon engineering or non-engineering factors (e.g. sales, marketing). In some embodiments, display 306 may integrated into computing device 300 or may be separate. In some embodiments, display 306 may be in virtually any size or resolution, such as a 4K resolution display, a microdisplay, one or more individual status or communication lights, e.g. LEDs, or the like.

In some embodiments of the present invention, acquisition device 310 may include one or more sensors, drivers, lenses and the like. The sensors may be visible light, infrared, and/or UV sensitive sensors, ultrasonic sensors, or the like, that are based upon any later-developed or convention sensor technology, such as CMOS, CCD, or the like. In some embodiments of the present invention, image recognition algorithms, image processing algorithms or other software programs for operation upon processor 302, to process the acquired data. For example, such software may pair with enabled hardware to provide functionality such as: facial recognition (e.g. Face ID, head tracking, camera parameter control, or the like); fingerprint capture/analysis; blood vessel capture/analysis; iris scanning capture/analysis; otoacoustic emission (OAE) profiling and matching; and the like. In additional embodiments of the present invention, acquisition device 310 may provide user input data in the form of a selfie, biometric data, or the like.

In various embodiments, audio input/output 312 may include conventional microphone(s)/speakers. In various embodiments, voice processing and/or recognition software may be provided to applications processor 302 to enable the user to operate computing device 300 by stating voice commands. In various embodiments of the present invention, audio input 312 may provide user input data in the form of a spoken word or phrase, or the like, as described above. In some embodiments, audio input/output 312 may be integrated into computing device 300 or may be separate.

In various embodiments, wired interface 314 may be used to provide data or instruction transfers between computing device 300 and an external source, such as a computer, a remote server, a POS server, a local security server, a storage network, another computing device 300, a client device, a peripheral device to control (e.g. a security door latch, a turnstile latch, a gate, a status light, etc.), or the like. Embodiments may include any later-developed or conventional physical interface/protocol, such as: USB, micro USB, mini USB, USB-C, Firewire, Apple Lightning connector, Ethernet, POTS, custom dock, or the like. In some embodiments, wired interface 314 may also provide electrical power, or the like to power source 324, or the like. In other embodiments interface 314 may utilize close physical contact of device 300 to a dock for transfer of data, magnetic power, heat energy, light energy, laser energy or the like. Additionally, software that enables communications over such networks is typically provided.

In various embodiments, a wireless interface 316 may also be provided to provide wireless data transfers between computing device 300 and external sources, such as computers, storage networks, headphones, microphones, cameras, or the like. As illustrated in FIG. 3, wireless protocols may include Wi-Fi (e.g. IEEE 802.11 a/b/g/n, WiMAX), Bluetooth, Bluetooth Low Energy (BLE) IR, near field communication (NFC), ZigBee, Ultra-Wide Band (UWB), Wi-Fi, mesh communications, and the like.

GPS receiving capability may also be included in various embodiments of the present invention. As illustrated in FIG. 3, GPS functionality is included as part of wireless interface 316 merely for sake of convenience, although in implementation, such functionality may be performed by circuitry that is distinct from the Wi-Fi circuitry, the Bluetooth circuitry, and the like. In various embodiments of the present invention, GPS receiving hardware may provide user input data in the form of current GPS coordinates, or the like, as described above.

Additional wireless communications may be provided via RF interfaces in various embodiments. In various embodiments, RF interfaces 320 may support any future-developed or conventional radio frequency communications protocol, such as CDMA-based protocols (e.g. WCDMA), GSM-based protocols, HSUPA-based protocols, G4, G5, or the like. In some embodiments, various functionality is provided upon a single IC package, for example the Marvel PXA330 processor, and the like. As described above, data transmissions between a smart device and the services may occur via Wi-Fi, a mesh network, 5G, 4G or the like.

In various embodiments, any number of future developed, current operating systems, or custom operating systems may be supported, such as iPhone OS (e.g. iOS), Google Android, Linux, Windows, MacOS, or the like. In various embodiments of the present invention, the operating system may be a multi-threaded multi-tasking operating system. Accordingly, inputs and/or outputs from and to display 306 and inputs/or outputs to physical sensors 322 may be processed in parallel processing threads. In other embodiments, such events or outputs may be processed serially, or the like. Inputs and outputs from other functional blocks may also be processed in parallel or serially, in other embodiments of the present invention, such as acquisition device 310 and physical sensors 322.

In some embodiments of the present invention, physical sensors 322 (e.g. MEMS-based) accelerometers, gyros, magnetometers, pressure sensors, temperature sensors, imaging sensors (e.g. blood oxygen, heartbeat, blood vessel, iris data, etc.), thermometer, otoacoustic emission (OAE) testing hardware, and the like may be provided. Embodiments or such smart devices described herein include smart rings, earbuds, smart glasses, smart watches, and the like, that typically include sensors contact or see the user's skin. The data from such sensors may be used to capture data associated with device 300, and a user of device 300. Such data may include physical motion data, pressure data, orientation data, or the like. Data captured by sensors 322 may be processed by software running upon processor 302 to determine characteristics of the user, e.g. gait, gesture performance data, or the like and used for user authentication purposes. In some embodiments, sensors 322 may also include physical output data, e.g. vibrations, pressures, and the like.

In some embodiments, a power supply 324 may be implemented with a battery (e.g. LiPo), ultracapacitor, or the like, that provides operating electrical power to device 300. In various embodiments, any number of power generation techniques may be utilized to supplement or even replace power supply 324, such as solar power, liquid metal power generation, thermoelectric engines, rf harvesting (e.g. NFC) or the like.

FIG. 3 is representative of components possible for a smart reader, a smart device, an authentication service server, a transaction service server, and the like for embodying different embodiments. It will be readily apparent to one of ordinary skill in the art that many other hardware and software configurations are suitable for use with the present invention. Embodiments of the present invention may include at least some but need not include all of the functional blocks illustrated in FIG. 3. For example, a smart phone (e.g. access control device) configured to perform may of the functions described above includes most if not all of the illustrated functionality. As another example, a wearable device, e.g. a smart ring (electronic devices enclosed in a ring-shaped shell, enclosure, or form factor), may include some of the functional blocks in FIG. 3, but it need not include a high-resolution display 330 or a touch screen, a speaker/microphone 360, wired interfaces 314, or the like. In still other examples, a cloud-based server or a virtual machine (VM) may not include image acquisition device 312, MEMS devices 322, GPS capability 316, and the like, further components described above may be distributed among multiple computers, virtual machines, or the like.

Therefore, it is to be understood that the present disclosure is not to be limited to the specific examples illustrated and that modifications and other examples are intended to be included within the scope of the appended claims. Moreover, although the foregoing description and the associated drawings describe examples of the present disclosure in the context of certain illustrative combinations of elements and/or functions, it should be appreciated that different combinations of elements and/or functions may be provided by alternative implementations without departing from the scope of the appended claims. Accordingly, parenthetical reference numerals in the appended claims are presented for illustrative purposes only and are not intended to limit the scope of the claimed subject matter to the specific examples provided in the present disclosure.

Further embodiments can be envisioned to one of ordinary skill in the art after reading this disclosure. In other embodiments, combinations or sub-combinations of the above disclosed invention can be advantageously made. The block diagrams of the architecture and flow charts are grouped for ease of understanding. However, it should be understood that combinations of blocks, additions of new blocks, re-arrangement of blocks, and the like are contemplated in alternative embodiments of the present invention.

The specification and drawings are, accordingly, to be regarded in an illustrative rather than a restrictive sense. It will, however, be evident that various modifications and changes may be made thereunto without departing from the broader spirit and scope of the invention as set forth in the claims. More specifically, the claims provide additional disclosure regarding contemplated additional methods of operation, methods for fabrication, additional components and functionalities, and apparatus according to various embodiments of the present invention.

We claim:

1. A smart ring comprises:
   a round shell comprising an external surface, an internal surface, and sidewalls, wherein the external surface defines an outer diameter portion of the smart ring, and wherein the internal surface and the sidewalls bound an interior region that is characterized by a u-shaped cross-section;
   a curved power source disposed within the interior region and within a first annulus sector of the smart ring, wherein the curved power source is configured to provide operating power;
   a circuit board coupled to the curved power source and disposed within the interior region and within a second annulus sector of the smart ring;

a plurality of electronic components disposed upon the circuit board, wherein the plurality of electronic components comprises:

a temperature sensor configured to provide a plurality of output signals in response to a heat source coupled to the temperature sensor;

a fingerprint sensor configured to provide incoming fingerprint data in response to a fingerprint provided to the fingerprint sensor;

a memory configured to store authorized fingerprint data; and a processing unit coupled to the temperature sensor and the fingerprint sensor, wherein the processing unit is configured to determine whether the incoming fingerprint data is authenticated in response to the authorized fingerprint data; and a potting compound disposed within the interior region and encapsulating the curved power source, the circuit board and the plurality of electronic components, wherein the potting compound forms an inner portion of the smart ring, wherein the interior portion of the smart ring is characterized by a first curved portion, a first flat region within a first portion of the second annulus sector, a second flat region within a second portion of the second annulus sector, and a third portion of the second annulus sector disposed between the first flat region and the second flat region;

wherein the fingerprint sensor is disposed below the first flat region; and wherein the temperature sensor is associated with the second flat region.

2. The smart ring of claim 1
wherein the fingerprint sensor comprises an ultrasonic sensor; and
wherein the fingerprint sensor is covered by the potting compound within the first flat region.

3. The smart ring of claim 1
wherein the fingerprint sensor is selected from a group consisting of: an imaging sensor and an infrared sensor; and
wherein the fingerprint sensor is exposed through the potting compound within the first flat region.

4. The smart ring of claim 1 further comprising:
one or more contacts coupled to the temperature sensor, wherein the one or more contacts are configured to thermally conduct heat to the temperature sensor; and
wherein the plurality of contacts are exposed through the potting compound within the second flat region.

5. The smart ring of claim 1
wherein the temperature sensor is selected from a group consisting of: an infrared device, and a near infrared device;
wherein a transparent material is disposed above the temperature sensor; and
wherein the transparent material is exposed through the potting compound within the second flat region.

6. The smart ring of claim 1 further comprising
an electromagnetic coil disposed below the first flat region, wherein the electromagnetic coil is configured to receive communications from an external electromagnetic source, and wherein the electromagnetic coil is covered by the potting compound within the first flat region.

7. The smart ring of claim 1 wherein the shell comprises a material selected from a group consisting of: plastic, ceramic, metal, silicone, titanium, non-conductive material, and carbon fiber.

8. The smart ring of claim 1 wherein the potting compound is selected from a group consisting of: epoxy, silicone, and rubber; and wherein the potting compound is over molded over the circuit board and the plurality of electronic components.

9. The smart ring of claim 1
wherein the memory is configured to store a digitally signed token;
wherein the plurality of electronic components further includes a first transceiver configured to output the digitally signed token.

10. The smart ring of claim 9 wherein the first transceiver comprises a Bluetooth low energy (BLE) transceiver.

11. A method for fabricating a smart ring comprises:
receiving a round shell comprising an external surface, an internal surface, and sidewalls, wherein the external surface defines an outer diameter portion of the smart ring, and wherein the internal surface and the sidewalls bound an interior region that is characterized by a u-shaped cross-section;

receiving a curved power source configured to provide operating power;

receiving a circuit board having a plurality of electronic components comprising:

a fingerprint sensor configured to provide incoming fingerprint data in response to a fingerprint provided to the fingerprint sensor;

a temperature sensor coupled to the curved power supply, wherein the temperature sensor is configured to determine a temperature associated with a user;

a memory configured to store authorized fingerprint data; and a processing unit coupled to the temperature sensor and the fingerprint sensor, wherein the processing unit is configured to determine whether the incoming fingerprint data is authenticated in response to the authorized fingerprint data;

coupling the curved power source to the circuit board;

disposing the curved power source within the interior region within a first annulus sector of the smart ring and the circuit board within a second annulus sector of the smart ring;

disposing the round shell within a mold; and disposing a potting compound into the mold to thereby encapsulate the curved power source and the circuit board, wherein the potting compound forms an inner portion of the smart ring, wherein the interior portion of the smart ring is characterized by a first curved portion, a first flat region within a first portion of the second annulus sector, a second flat region within a second portion of the second annulus sector, and a third portion of the second annulus sector disposed between the first flat region and the second flat region;

wherein the fingerprint sensor is disposed below the first flat region; and wherein the temperature sensor is associated with the second flat region.

12. The method of claim 11
wherein the fingerprint sensor comprises an ultrasonic sensor; and
wherein the potting compound is disposed above the ultrasonic sensor within the first flat region.

13. The method of claim 11
wherein the fingerprint sensor is selected from a group consisting of: an imaging sensor and an infrared sensor; and wherein the potting compound exposes the fingerprint sensor within the first flat region.

14. The method of claim 11 further comprising:

coupling a thermal contact to the temperature sensor, wherein the thermal contact is configured to thermally convey heat to the temperature sensor; and wherein the potting compound exposes the thermal contact within the second flat region.

15. The smart ring of claim 11 wherein the temperature sensor is selected from a group consisting of: an infrared device, and a near infrared device; and wherein the method further comprises disposing a transparent material above the temperature sensor; and wherein the transparent material is exposed through the potting compound within the second flat region.

16. The method of claim 11 further comprising molding the round shell with a material selected from a group consisting of: plastic, ceramic, metal, silicone, titanium, non-conductive material, and carbon fiber.

17. The method of claim 11 wherein the potting compound is selected from a group consisting of: epoxy, silicone, and rubber; and wherein the disposing the potting compound comprises over molding the circuit board and the plurality of electronic components.

18. The method of claim 11 wherein the coupling the curved power source to the circuit board comprises coupling a first end of the curved power source to a first end of the circuit board; and wherein the disposing the curved power source and the circuit board within the interior region comprises:

overlapping a second end of the curved power source to a second end of the circuit board into an O-shaped configuration;

disposing the curved power source and the circuit board in the O-shaped configuration into the interior region; and unoverlapping the second end of the curved power source from the second end of the circuit board into an C-shaped configuration.

19. The method of claim 18 further comprising:

securing a registration frame within the interior region; and coupling at least a portion of the circuit board or the curved power source to the registration frame within the interior region.

20. The method ring of claim 19 wherein the registration frame comprises a magnetic material.

* * * * *